United States Patent [19]

Winstel et al.

[11] 3,999,122

[45] Dec. 21, 1976

[54] SEMICONDUCTOR SENSING DEVICE FOR FLUIDS

[75] Inventors: Guenter Winstel, Ottobrunn; Johannes Rachmann, Munich, both of Germany

[73] Assignee: Siemens Aktiengesellschaft, Berlin & Munich, Germany

[22] Filed: Feb. 14, 1975

[21] Appl. No.: 549,893

[30] Foreign Application Priority Data

Feb. 14, 1974 Germany ............................ 2407110

[52] U.S. Cl. .............................. 324/71 SN; 73/27 R; 200/61.04; 23/232 E; 338/13; 23/230 B; 23/254 E

[51] Int. Cl.² ........................................ G01N 27/52

[58] Field of Search ................ 324/71 SN; 357/25; 338/13, 34; 73/28

[56] References Cited

UNITED STATES PATENTS

| | | | |
|---|---|---|---|
| 3,045,198 | 7/1962 | Dolan et al. | 338/13 |
| 3,255,324 | 6/1966 | Ovshinsky | 200/61.04 |
| 3,428,892 | 2/1969 | Meinhard | 324/71 SN |
| 3,831,432 | 8/1974 | Cox | 73/23 |
| 3,865,550 | 2/1975 | Bott et al. | 23/232 E |

*Primary Examiner*—Robert Segal
*Assistant Examiner*—Vincent J. Sunderdick
*Attorney, Agent, or Firm*—Hill, Gross, Simpson, Van Santen, Steadman, Chiara & Simpson

[57] ABSTRACT

A semiconductor sensor for fluids comprised of a body composed of an inorganic semiconductor material which is provided with a drain and source zone interconnected by a channel zone and including a layer of a reactive organic material capable of forming a reversible bond with at least a portion of the fluid being detected in the vicinity of the channel zone between the source and drain zones. The reactive organic material, such as carotenoids, polypropylenes, phthalocyanines, etc. reversably interacts with molecules of a given fluid substance and produce a reversible change in the surface potential of the layer composed of the organic material via a field effect and thus produce a reversible change of resistance in the channel zone and indicates the presence of such fluid by a change in the drain current of the sensor.

16 Claims, 2 Drawing Figures

SEMICONDUCTOR SENSING DEVICE FOR FLUIDS

BACKGROUND OF THE INVENTION

Field of the Invention

The invention relates to sensors for detecting fluids such as gases or liquids and somewhat more particularly to a semiconductor sensor comprised of a body of an inorganic semiconductor material having a source, a drain and a channel zone therebetween so that the presence of a given fluid is detectable by a change in the drain current of the sensor.

Prior Art

J. Electrochemical Soc.; "Solid-State Science and Technology," Vol. 119, October 1972, pages 1424–1425, suggests a sensor device comprised of a Si body coated with a natural oxide layer and having drain and source zones interconnected with one another via a channel zone, without a gate electrode, so that a change in the current-voltage characteristic of the device occurs when it is submerged in an organic liquid due to the emission of charge carriers therefrom into the channel zone.

"Soap Perfumery & Cosmetics," Vol. 37, 1964, pages 38–41, suggests a sensor device wherein two thermistors are arranged in a bridge circuit, one of which is coated with a layer of an organic material and a de-tuning of the bridge occurs in the presence of odoriferous fluids due to release of adsorption heat created by the inner action of the organic material and such odoriferous fluids.

"Biochemical-Biophysical Acta," Vol. 148, 1967, pages 328–334, mentions that $\beta$-carotene occurs in certain biological olfactory systems.

The heretofore described sensor devices have an insufficient selectivity and/or reversibility. Further, these prior art systems also show a reduced sensitivity after a multiple usage period, i.e. they are subject to fatigue.

SUMMARY OF THE INVENTION

The invention provides a semiconductor sensor device for fluid substances capable of reversible operation at room temperatures with a recovery time of 1 to 10 minutes and having a high degree of selectivity and sensitivity.

In accordance with the principles of the invention, a semiconductor body composed of an inorganic semiconductor material, such as Si, Ge, Ga, etc. is provided with a source-, a drain- and a channel zone interconnecting the source and drain zones. A relatively thin layer of an organic material, such as a carotenoid, for example, $\beta$-carotene, a protein, a phthalocyanine, a polyvinyl chloride, a polypropylene, a cellulose acetate, etc., which is reversibly reactive with select fluid substances is positioned within the region of the channel zone so that upon interaction (adsorption and/or desorption) of the organic material with minute amounts of a fluid substance, a reversible change in the surface potential of the layer occurs due to a field effect and causes a reversible change in the resistance of the channel zone which is detected by a change in the drain current of the semiconductor sensor.

In certain embodiments of the invention, a selectively permeable filter or membrane is positioned above the layer of reactive organic material so that only such fluid substances which permeate the filter are detected by the so-constructed sensor. In other embodiments, a plurality of sensors are provided with different reactive layers so that characteristic changes in drain current of the individual sensors occur for various fluid substances being monitored or detected.

DESCRIPTION OF THE PREFERRED EMBODIMENTS

The invention provides a semiconductor field effect sensor for fluid substances capable of reversible operation at room temperatures with relaxation or recovery times of 1 to 10 minutes and having a high degree of selectivity and sensitivity.

The field effect sensors of the invention are useful in a wide variety of environments and are particularly useful in detecting various gases, liquids, and impurities in ambient environments, such as $SO_2$, $CO$, $CO_2$, $N_xO_y$, $NH_3$, acetone and other fluid substances. The field sensors of the invention are useful, for example, in medical diagnoses of ventilating air, exhaled air, etc. and also in monitoring various industrial and/or agricultural processes.

The invention is based upon the principle that the adsorption energy at room temperatures is generally lower when fluid substances interact with organic materials than when they interact with inorganic materials. The degree of coverage of interaction between the odoriferous substance being detected by the organic material at a constant or relatively constant temperature and concentration reaches an equilibrium between the rate of adsorption and desorption. As a result of this equilibrium, a potential change occurs on the surface of the adsorptive layer (i.e. a layer of the organic material) which is characteristic of the degree of coverage of interaction of a given fluid substance. Such change of potential causes a change in the threshold voltage of a field effect sensor having such adsorptive or reactive layer therein. Consequently, the drain current of such a sensor is controlled or changed in relation to the degree of coverage or interaction between the fluid substance and the organic material.

In accordance with the invention, the detection sensitivity may be increased by decreasing the thickness dimension of the adsorption layer and/or by increasing the ratio of channel width to channel length on semiconductor sensor devices of the invention. In addition, the sensitivity of a sensor constructed in accordance with the principles of the invention for one type of molecule in comparison to other types of molecules may be increased by the judicious selection of an adsorption or reactive organic material so that it has a molecular construction or steric arrangement which forms or possesses a matrix on which molecules of the fluid substance being detected accumulate because of the substantial match between the structure of such molecules and the structure of the matrix of the reactive organic material. Further, selectivity of a sensor in accordance with the invention may also be achieved by the fact that with a given adsorption or reactive material, the change in drain current can be greater or smaller than zero for two different types of fluid molecules.

Figure 1:
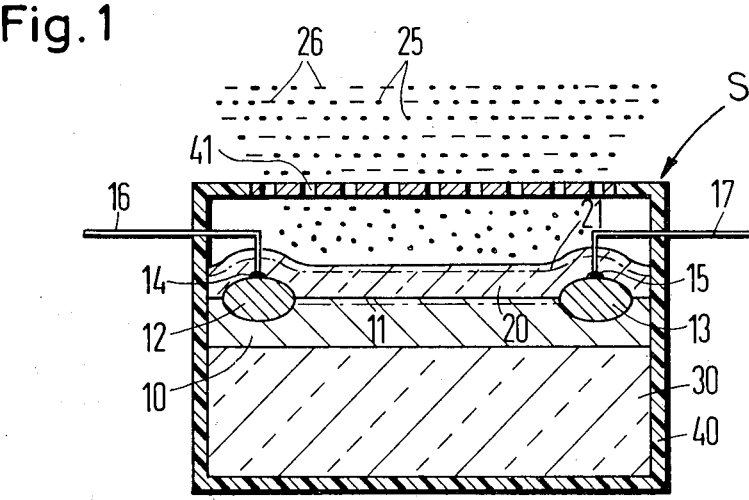
FIG. 1 is a cross-sectional elevated, somewhat schematic, view of an exemplary embodiment of a sensor device constructed and operating in accordance with the principles of the invention.

Referring now to FIG. 1, an exemplary sensor $S_1$ constructed in accordance with the principles of the invention is illustrated. Sensor $S_1$ is formed of a substrate 30 composed of an inorganic insulator material, for example, an Al-Mg spinel or the like and has an epitaxially deposited semiconductor layer 10 thereon. The semiconductor layer 10 is composed of an inorganic semiconductor material selected from the group consisting of Si, Ge, Ga, As, a III-V compound and a II-VI compound. A drain contact strip or zone 12 and a source contact or strip 13 are positioned on the layer 10 in a spaced-apart relation as shown. Any oxide layer which may be present on the inorganic semiconductor layer 10 should be as thin as possible. If the inorganic semiconductor layer 10 has a different conductivity type from that of the contact zones 12 and 13, a channel zone 11 having the conductivity type of the contact zones 12 and 13 is provided, as by implantation, in order to facilitate a "normally-on" operation of the sensor $S_1$. The operative surface, i.e. the upper surface, of the resultant structure is coated, as by vapor deposition, with a layer 20 of a highly ohmic organic material. The layer 20 is sometimes referred to hereinafter as a reactive or adsorption layer. Gold wires 16 and 17 of approximately $25\mu$ diameter are bonded onto the contact zones 12 and 13, respectively, at points 14 and 15 thereof. An insulating layer 40, for example, composed of Teflon (a registered trade mark for polytetrafluoroethylene) may be provided about the resultant structure so as to leave only the operative surface 21 of the adsorption layer 20 exposed to ambient environment.

In the embodiment illustrated at FIG. 1, a filter or membrane 41 is positioned above the operative surface 21. The filter or membrane 41 is permeable to only a few or just one type of molecule. For example, two types of molecules 25 and 26 are schematically illustrated above membrane 41 and only molecules 25 are permeable in either direction through the membrane 41. Such an arrangement provides an increased selectivity for a sensor which includes such a filter or membrane. Selectively permeable filters or membranes for gaseous or liquid fluid substances are known and depending upon the substances being detected or monitored, an appropriate filter may be selected.

The thickness of the adsorption layer 20 is controlled so as to be less than about 500 nm and preferably less than about 200 nm so that the sensitivity of the resultant sensor is particularly good. However, the layer 20 must have a sufficient thickness to be cohesive.

As, for example, molecules 25 reversably interact with the adsorption organic material on the operative or upper surface 21 of layer 20, a reversible surface potential change occurs via a field effect. This produces a reversible change of resistance in the channel zone 11 and a suitable meter or the like signals a change in the drain current of the sensor $S_1$, thereby indicating the presence of a given fluid substance (gas or liquid).

Figure 2:
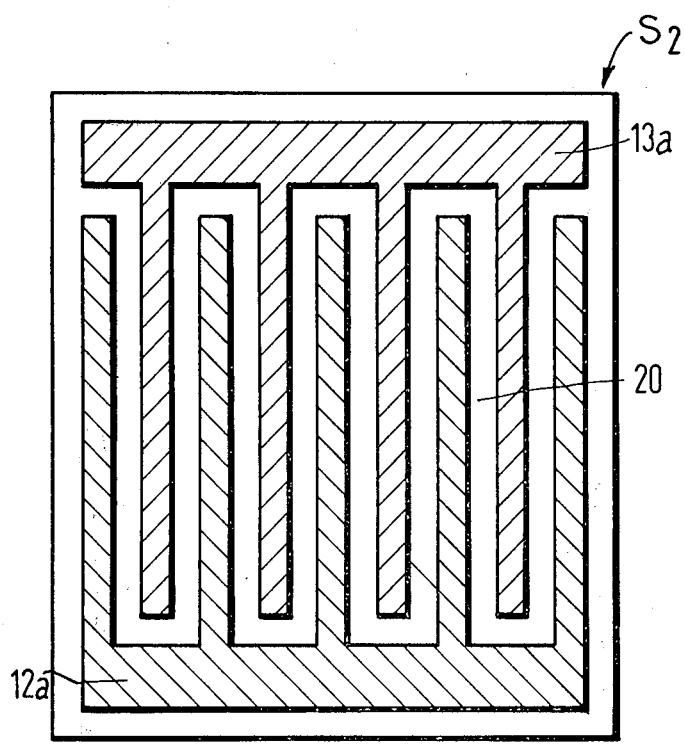
FIG. 2 is a cross-section of a plan view of another exemplary embodiment of a sensor device in accordance with the principles of the invention.

FIG. 2 illustrates another exemplary sensor $S_2$ constructed in accordance with the principles of the invention. The sensor $S_2$ is somewhat similar to sensor $S_1$ and comprises a field effect transistor without a gate electrode and with, for example, a diffused drain zone 12a and a diffused source zone 13a. As shown, the zones 12 and 13 are arranged so spaced-apart interdigital channels having a high ratio of channel width to channel length, thereby increasing the sensitivity of sensor $S_2$. A layer 20 of a reactive or adsorption organic material is provided on the field effect transistor for operation in the manner described in conjunction with sensor $S_1$.

In further exemplary embodiments of the invention, a plurality of sensors constructed in accordance with the principles of the invention may be combined with different adsorption layers so that characteristic changes in the drain current of the individual sensors occur for various fluid substances which are being detected or monitored. The total number of individual sensors which are so-combined does not have to be very great since the human sense of smell is, in fact, composed of only seven basic sensitivities. Such a combination of sensors, which may be thought of as an artificial nose, may, in certain embodiments, be designed so that it has an odor spectrum not only accessible to the human being but also to trace amounts of other substances not accessible to the human sense of smell.

The reactive or adsorption organic materials useful in forming the adsorption or reactive layer 20 of the invention may be organic substances or compounds per se or be organic semiconductors. Particularly useful organic materials in forming the reactive layer 20 may be selected from the group consisting of carotenoids, particulary $\beta$-carotene; proteins, phthalocyanines, polyvinyl chlorides, polypropylenes and cellulose acetates as well as mixtures thereof. The reactive organic material is preferably so selected that it is in the form of an organic compound which, because of its molecular structure or steric arrangement, forms or possesses a matrix on which gaseous particles (molecules), particularly organic particles of one or more fluid substances having a molecular structure matching the structure of the matrix, selectively accumulate and produce the desired electrical results.

With the foregoing general discussion in mind, there is presented hereinafter a detailed example which will illustrate to those skilled in the art the manner in which this invention is carried out. However, this example is not to be construed as limiting the scope of the invention in any way.

A field effect sensor is constructed substantially as shown in FIG. 1 but without a filter or membrane 41. The adsorption layer 20 comprises a vapor deposited and subsequently oxidized $\beta$-carotene of a thickness of 100 nm. The inorganic semiconductor body 10 is composed of Si which has a hole concentration of $p \approx 4 \times 10^{15}$ cm$^{-3}$. The so-constructed sensor is then connected to an electrical circuit having the means for monitoring the drain current thereof. Thereafter, a first gaseous mixture of carbon monoxide and nitrogen and a second gaseous mixture of acetone and nitrogen are brought into contact with the operational sensors and the changes in drain current noted. Changes in drain current were calculated in accordance with the equation:

$$[I(o) - I(p)]/I(p) \quad \Delta I_D/I_D$$

and the results obtained are as follows:

CO mixtures $p_{CO} \approx 10$ PA $\Delta (I_D/I_D) \approx 6.6°/$oo acetone mixture $p_{acetone} \approx 2.5 \times 10^4$ PA $\Delta (I_D/I_0) \approx 5.6°/$oo.

It is thought that the invention and its advantages will be understood from the foregoing description that it is apparent that various changes may be made in the process, form, construction and arrangement of the parts without departing from the spirit and scope of the invention or sacrificing its material advantages, the forms hereinbefore described and illustrated in the drawings being merely presently preferred exemplary embodiments.

We claim as our invention:

1. A sensor device for detecting fluid substances, comprising:
   a substrate of an inorganic insulating material,
   an epitaxially grown layer of an inorganic semiconductor material on a surface of said substrate,
   a source zone and a spaced-apart drain zone of a given conductivity type on said epitaxially grown layer and a channel zone of said conductivity type interconnecting said drain and source zones with one another,
   an electrical lead on each of said drain and source zones for interconnecting said sensor device with an operational electrical circuit,
   a relatively thin layer of a reactive organic material capable of reversible interaction with fluid substances being detected, said organic material being selected from the group consisting of carotenoids, proteins, phthalocyanines, polyvinyl chlorides, polypropylenes, cellulose acetate and mixtures thereof, said layer being in direct contact with a free surface of said epitaxially grown layer,
   whereby upon energization of said sensor device in the presence of a fluid substance, a reversible reaction occurs between said substance and said organic material and causes a reversible change in the surface potential of said layer due to a field effect and causes a reversible change in the resistance of said channel zone so that the drain current of said sensor is changed.

2. A sensor device as defined in claim 1 wherein said organic material is a carotenoid.

3. A sensor device as defined in claim 2 wherein said carotenoid is an oxidized $\beta$-carotene.

4. A sensor device as defined in claim 1 wherein said reactive organic material is a cellulose acetate.

5. A sensor device as defined in claim 1 wherein said reactive organic material is a protein.

6. A sensor device as defined in claim 1 wherein said reactive organic material is a phthalocyanine.

7. A sensor device as defined in claim 1 wherein said reactive organic material is a polyvinyl chloride.

8. A sensor device as defined in claim 1 wherein said reactive organic material is a polypropylene.

9. A sensor device as defined in claim 1 wherein said layer of reactive organic material is of a thickness less than 500 nm.

10. A sensor device as defined in claim 9 wherein said layer of reactive organic material is of a thickness less than 200 nm.

11. A sensor device as defined in claim 1 wherein said reactive organic material is reactive with liquid substances.

12. A sensor arrangement comprised of a plurality of sensors as defined in claim 1 wherein individual sensors are provided with layers of different reactive organic materials so that each such sensor is sensitive to different fluid substances.

13. A sensor device as defined in claim 1 wherein said drain and source zones comprise spaced-apart interdigital channels having a high ratio of channel width to channel length.

14. A sensor device as defined in claim 1 wherein said reactive organic material is reactive with gaseous substances.

15. A sensor device as defined in claim 14 wherein said reactive organic material is $\beta$-carotene and said gaseous substance is carbon monoxide.

16. A sensor device as defined in claim 11 wherein said reactive organic material is $\beta$-carotene and said fluid substance is acetone.

* * * * *